(12) United States Patent
Chang et al.

(10) Patent No.: US 9,566,410 B2
(45) Date of Patent: Feb. 14, 2017

(54) SLEEP AID SYSTEM AND OPERATION METHOD THEREOF

(71) Applicant: AmTRAN Technology Co., Ltd., New Taipei (TW)

(72) Inventors: Shao-Chin Chang, Taichung (TW); Hsu-Hsuan Wu, Taipei (TW)

(73) Assignee: AmTRAN Technology Co., Ltd., New Taipei (TW)

(*) Notice: Subject to any disclaimer, the term of this patent is extended or adjusted under 35 U.S.C. 154(b) by 197 days.

(21) Appl. No.: 14/582,135

(22) Filed: Dec. 23, 2014

(65) Prior Publication Data
US 2015/0187199 A1 Jul. 2, 2015

(30) Foreign Application Priority Data
Dec. 30, 2013 (TW) .............................. 102149084 A

(51) Int. Cl.
*A61M 21/00* (2006.01)
*A61M 21/02* (2006.01)
(Continued)

(52) U.S. Cl.
CPC .............. *A61M 21/02* (2013.01); *A61B 5/048* (2013.01); *A61B 5/4809* (2013.01);
(Continued)

(58) Field of Classification Search
CPC ... A61B 5/4806; A61B 5/4809; A61B 5/4812; A61B 5/4818; A61B 5/74; A61B 5/7405; A61B 5/742; A61B 19/34; A61B 19/3418; A61B 18/3431; G06F 19/34; G06F 19/3418; G06F 19/3431; A61M 21/00; A61M 2021/0005; A61M 2021/0027; A61M 21/02
See application file for complete search history.

(56) References Cited

U.S. PATENT DOCUMENTS 6,488,617 B1   12/2002   Katz
7,689,274 B2    3/2010   Mullen et al.
(Continued)

FOREIGN PATENT DOCUMENTS

CN   101111842 A   1/2008
CN   201828822 U   5/2011
(Continued)

*Primary Examiner* — Van Trieu
(74) *Attorney, Agent, or Firm* — CKC & Partners Co., Ltd.

(57) ABSTRACT

A sleep aid system and an operation method thereof are disclosed. The sleep aid system includes a sleep aid device including a retrieving module, a processing module, and a transmitting module, and a server. The retrieving module retrieves a brainwave signal including specific frequency band signals. The processing module analyzes the brainwave signal to obtain an index in each of the specific frequency band signals and calculates a sleepless degree parameter representing one of at least five brainwave states regarding sleep accordingly. The transmitting module transmits a parameter signal corresponding to the sleepless degree parameter. The server receives the parameter signal from the transmitting module. The server stores comparison data, compares the parameter signal to the comparison data, and generates a first feedback signal according to a comparison result. The first feedback signal includes a command to switch an audio file or stream which is currently being played.

20 Claims, 7 Drawing Sheets

(51) Int. Cl.
*A61B 5/00* (2006.01)
*A61B 5/048* (2006.01)

(52) U.S. Cl.
CPC .......... *A61B 5/6898* (2013.01); *A61B 5/4812* (2013.01); *A61M 2021/005* (2013.01); *A61M 2021/0027* (2013.01)

(56) References Cited

U.S. PATENT DOCUMENTS

| | | |
|---|---|---|
| 8,213,670 B2 | 7/2012 | Lai |
| 8,961,413 B2* | 2/2015 | Teller ................ A61B 5/02055 600/301 |
| 2011/0010014 A1* | 1/2011 | Oexman .............. A47C 27/061 700/276 |
| 2011/0160524 A1 | 6/2011 | Ni et al. |
| 2013/0190556 A1* | 7/2013 | Wetmore ............... G09B 19/00 600/28 |

FOREIGN PATENT DOCUMENTS

| | | |
|---|---|---|
| CN | 102114303 A | 7/2011 |
| JP | 2008533504 A | 8/2008 |
| JP | 2009233027 A | 10/2009 |

\* cited by examiner

SLEEP AID SYSTEM AND OPERATION METHOD THEREOF

RELATED APPLICATIONS

This application claims priority to Taiwanese Patent Application Serial Number 102149084, filed Dec. 30, 2013, which is herein incorporated by reference.

BACKGROUND

Field of Invention

The present invention relates to a sleep aid system and an operation method thereof. More particularly, the present invention relates to a sleep aid system and an operation method thereof in order to create a comfortable sleep environment.

Description of Related Art

Having quality sleep is vital to one's health. In general, it's easier for people to fail asleep in a comfortable and familiar environment. Some people may like to watch television program or listen to music in bed in order to aid sleep.

However, a person who is nearly asleep can be awoken or disturbed because the television screen nearby is too bright or the playing music is too loud, etc. In other cases, the playing music might not help the person to enter into sleep when the person is trying to sleep. In summary, people may lose the feeling of sleepiness easily due to environmental factors, and therefore sleep disorder problems are caused.

Accordingly, a system for establishing or improving a comfortable sleep environment is strongly needed, so as to help a person to smoothly enter into sleep.

SUMMARY

The present invention provides a sleep aid system. The sleep aid system comprises a sleep aid device and a server. The sleep aid device comprises a retrieving module, a processing module and a transmitting module. The retrieving module retrieves a brainwave signal and the brainwave signal comprises a plurality of specific frequency band signals. The processing module analyzes the brainwave signal in order to obtain an index in each of the plurality of specific frequency band signals, and the processing module calculates a sleepless degree parameter according to the index in each of the plurality of specific frequency band signals, wherein the sleepless degree parameter represents one of at least five brainwave states regarding sleep. The transmitting module transmits a parameter signal corresponding to the sleepless degree parameter. The server receives the parameter signal from the transmitting module. The server stores a multiple sets of comparison data. The server compares the parameter signal to the comparison data and generates a first feedback signal according to a comparison result. The first feedback signal comprises a command to switch an audio file or stream which is currently being played to other audio file or stream.

In one aspect, the present invention is directed to provide a sleep aid system. The sleep aid system comprises a sleep aid device and an electronic device. The sleep aid device comprises a retrieving module, a processing module and a transmitting module. The retrieving module retrieves a brainwave signal and the brainwave signal comprises a plurality of specific frequency band signals. The processing module analyzes the brainwave signal in order to obtain an index in each of the plurality of specific frequency band signals, and calculates a sleepless degree parameter according to the index in each of the plurality of specific frequency signals, wherein the sleepless degree parameter represents one of at least five brainwave states regarding sleep. The transmitting module transmits a parameter signal corresponding to the sleepless degree parameter to a server. The electronic device plays an audio file or stream. The electronic device transmits audio associated data to the server and receives a first feedback signal from the server. The electronic device switches a currently played audio file or stream according to the first feedback signal.

In anther aspect, the present invention is directed to provide a sleep aid system. The sleep aid system comprises a sleep aid device and a server. The sleep aid device comprises a retrieving module, a processing module and a transmitting module. The retrieving module retrieves a brainwave signal and the brainwave signal comprises a plurality of specific frequency band signals. The processing module analyzes the brainwave signal in order to obtain an index in each of the plurality of specific frequency band signals and calculates a sleepless degree parameter according to the index in each of the plurality of specific frequency band signals, wherein the sleepless degree parameter represents one of at least five brainwave states regarding sleep. The transmitting module transmits a parameter signal corresponding to the sleepless degree parameter. The server receives the parameter signal from the transmitting module. The server determines a state of the brainwave signal according to the parameter signal. The server generates a first feedback signal when the brainwave signal is determined as entering an asleep state. The first feedback signal comprises a command to turn off a display device.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE EMBODIMENTS

Figure 1A:
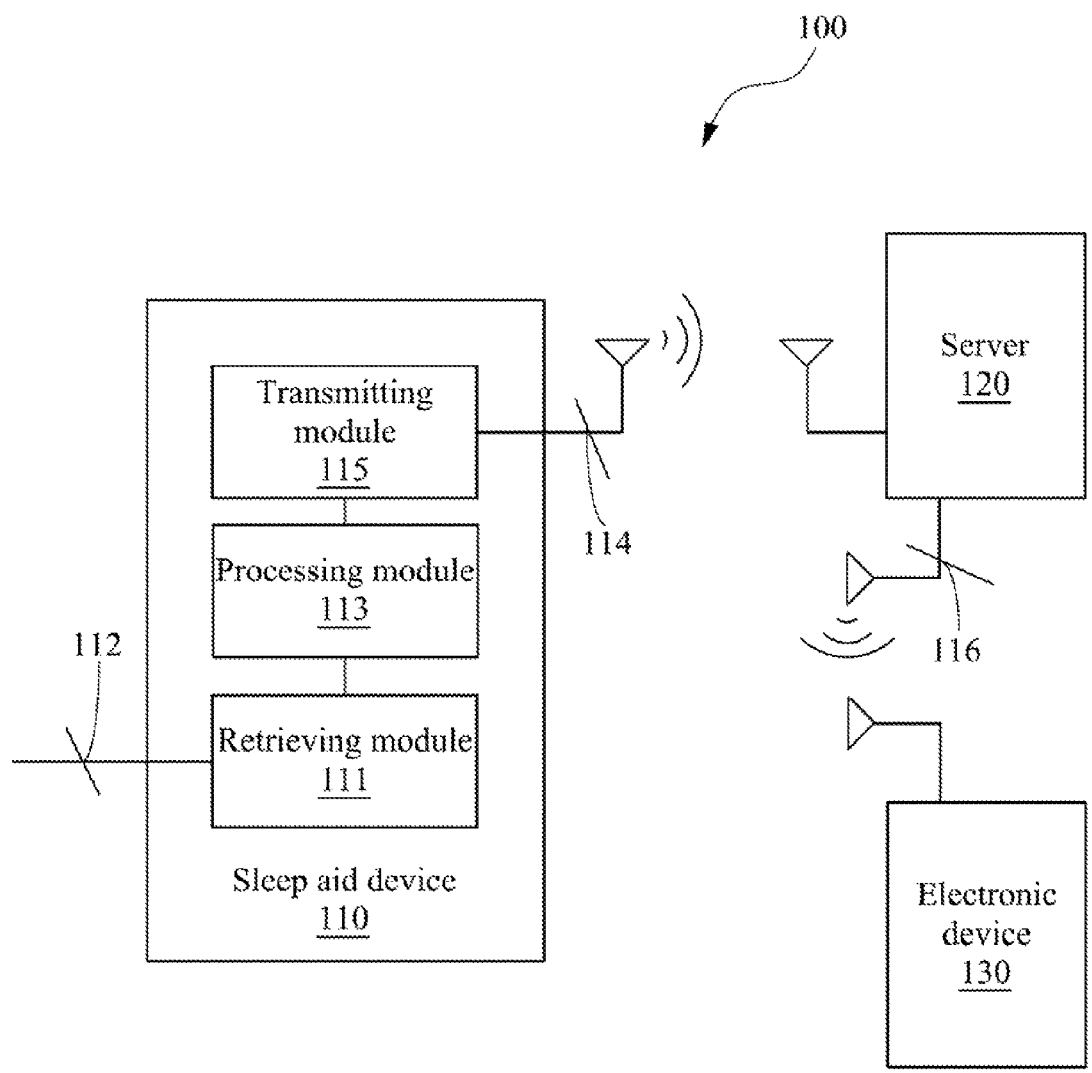
FIG. 1A is a diagram illustrating a sleep aid system according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

Reference is now made to FIG. 1A. FIG. 1A is a diagram illustrating a sleep aid system 100 according to an embodiment of the present invention.

In the present embodiment, the sleep aid system 100 includes a sleep aid device 110 and a server 120. The sleep aid device 110 can detect a brainwave signal 112 of a user, and then calculates a sleepless degree parameter of the user accordingly. The server 120 can receive a parameter signal 114 corresponding to the sleepless degree parameter of the user, and then compares the parameter signal 114 to a plurality of parameter data. In order to help the user enter into sleep, the server 120 transmits a feedback signal 116 to an electronic device 130 which makes the electronic device 130 play an audio file or stream suitable for aiding the user's sleep.

As shown in FIG. 1A, the sleep aid device 110 includes a retrieving module 111, a processing module 113 and a transmitting module 115. The processing module 113 is electrically connected to the retrieving module 111 and the transmitting module 115, so as to receive a signal transmitted from the retrieving module 111 and output a processed signal via the transmitting module 115.

In specific, the sleep aid device 110 can be a headset device made of a soft or elastic material, so that when a user wears the sleep aid device 110, the sleep aid device 110 does not interfere with the user's sleep. In addition, the sleep aid device 110 is not limited to be a headset device, and can be any device which includes detecting nodes of physiological signals. The detecting nodes can be attached to the skin of the user's head in order to detect and provide physiological signals for the retrieving module 111. The detecting nodes passively detect physiological signals on the user's head, including at least a physiological signal detected at a position relatively close to brain and another physiological signal detected at a position relatively further away from the brain. The retrieving module 111 compares and eliminates noises and unrelated parts in the physiological signals according to the physiological signal detected at different positions by the detection nodes, so as to retrieve a brainwave signal 112. The brainwave signal 112 includes a plurality of specific frequency band signals.

For instance, the brainwave signal represents the current activities of a brain, including at least θ wave, α wave and β wave signals. Frequency bands of the θ wave, the α wave and the β wave are ranged in between 3-7 Hertz (Hz), 8-12 Hz and 18-30 Hz respectively. In other words, the retrieving module 111 performs signal amplification, normalization and noise elimination to the retrieved brainwave signal 112 and obtains specific frequency band signals such as the θ wave, the α wave and the β wave, etc., from the brainwave signal 112.

The processing module 113 then analyzes the brainwave signal 112, so as to obtain an index in each of the plurality of specific frequency band signals. The processing module 113 calculates a sleepless degree parameter according to the indexes of the specific frequency band signals.

Reference is now made to Table 1. Table 1 is a table illustrating indexes representing specific frequency band signals in brainwave signals of different users in one embodiment of the present invention.

TABLE 1

Indexes of specific frequency band signals in brainwave signals

|  | θ wave (3-7 Hz) | α wave (8-12 Hz) | β wave (18-30 Hz) |
| --- | --- | --- | --- |
| User A | 7x | 7y | 2z |
| User B | 5x | 6y | 3z |
| User C | 4x | 7y | 2z |
| User D | 3x | 4y | 6z |
| User E | 3x | 4y | 7z |

Indexes shown in Table 1 represent sleepless status of different users. For instance, each of users A-E wears a sleep aid device 110 respectively and the retrieving module 111 of the sleep aid device 110 retrieves a brainwave signal 112 of each of the users A-E in real-time. The processing module 113 of the sleep aid device 110 then start analyzing brainwave signals 112 of the users A-E and obtains indexes corresponding to specific frequency band signals of the θ wave, the α wave and the β wave, etc., respectively. For example, the indexes are ranged in between 0-10x, 0-10y and 0-10z respectively, where x, y and z are general coefficients. The above-mentioned indexes are obtained after normalizing each frequency band of brainwave signals, and the normalized indexes can be used to presume as the brainwave signal in each frequency band of each user. For instance, after the brainwave signals of the user A in Table 1 are processed, the signals in θ wave, α wave, and β wave bands of the user A is approximately in the ratio of 7:7:2, and a sleepless degree parameter corresponding to the user A at the time can be calculated according to the indexes. Please note that the numbers representing each index here are merely for exemplary purposes and are not meant to limit the scope of the present invention. Any technology that is capable of generating an index according to a brainwave signal is within the scope of the present invention.

Reference is now again made to Table 1. The indexes corresponding to specific frequency band signals θ wave, the α wave and the β wave in the brainwave signal 112 of the user B are 5x, 6y and 3z respectively. The processing module 113 of the sleep aid device 110 can calculate sleepless degree parameters of the user B as the table 2 below according to the indexes of the θ wave signal, the α wave signal and the β wave signal.

TABLE 2

Sleepless degree category and the corresponding state

| Sleepless degree category (Rank) | Sleepless degree parameter (Score) | Corresponding state |
| --- | --- | --- |
| 1 | 0~15 | Almost asleep |
| 2 | 15~20 | A bit sleepy |
| 3 | 20~30 | Almost asleep but wakes up again |
| 4 | 30~60 | Wants to sleep but unable to |
| 5 | 60~100 | Busy mind |

Please note that the sleepless degree parameter mentioned above can represent a sleepless degree or state of a user. For instance, as shown in Table 2, the sleepless degree category 1, having a sleepless degree parameter of 0-15, indicates the user is in the "Almost asleep" state, i.e. the closest state to sleep. The sleepless degree category 2, having a sleepless degree parameter of 15-20, indicates the user is in the "A bit sleepy" or half awake state. The sleepless degree category 3, having a sleepless degree parameter of 20-30, indicates the user is in the "Almost asleep but wakes up again" state. The sleepless degree category 4, having a sleepless degree parameter of 30-60, indicates the user is in the "Wants to sleep but unable to" state. The sleepless degree category 5, having a sleepless degree parameter of 60-100, indicates the user is in the "Busy mind" state. However, the above-mentioned indexes of the brainwave signal and the sleepless degree parameters are merely for exemplary purposes and are not meant to limit the scope of the present invention.

In the present embodiment, the server 120 stores multiple sets of comparison data. The comparison data includes past brainwave variation records of a user and audios previously played corresponding to the brainwave variation records. The comparison data can also include the location records of the user, the time records or other identification or physiological data of the user. The sleep aid device 110 instantly transmits the parameter signal 114 which corresponds to a sleepless degree parameter of the user to the server 120 wirelessly via the transmitting module 115. The server 120 also receives the parameter signal 114 from the transmitting module 115, compares the parameter signal 114 to the stored comparison data, and then determines whether to generate a feedback signal 116 according to a comparison result, wherein the feedback signal 116 is generated to switch the currently played audio file or stream to any other audio file or stream or play a specific audio file or stream instantly. The feedback signal 116 includes a command to switch an audio file or stream which is currently being played by the sleep aid device 110 or other audio playback device to other audio file or stream. For instance, when a user's brainwave status is unable to enter into sleep for a period of time, or the brainwave status even changes towards a more conscious or sleepless degree category, the server 120 will generate the feedback signal 116 to command the audio playback device to change the currently played audio file or stream. Such action corresponds to the above-mentioned command to switch an audio file or stream which is currently being played to any other audio file or stream. Alternatively, when the server 120 determines the user's brainwave status has stayed in a particular sleepless degree category and not changed for a certain period of time, the server 120 can select an audio file or stream that is most effective in helping the user enter into sleep in this particular sleepless degree category based the history records of the user, and a feedback signal 116 is generated to command the playback device to play such specific audio file or stream. At any time, the server 120 can compare the history records of a user or user group based on factors, such as current sleepless degree category of the user, or current system time . . . , etc, and select a specific audio file or stream that is most effective in aiding the user's sleep, or set the priorities of any playable audio file or streams and then select an audio file or stream with higher priorities, so that the feedback signal 116 can be generated to command the playback device to play the selected audio file or stream. In other words, the specific audio file or stream which is going to be played is determined by the server 120 based on the comparison data and the parameter signal 114.

In an embodiment of the present invention, the server 120 can transmit the feedback signal 116 to the electronic device 130, which includes the playback device, through wireless transmission in real-time, so as to control the electronic device 130 to play a specific audio file or stream to the user. The server 120 then keeps track of the sleepless degree parameter from the user listening to the specific audio file or stream simultaneously according to the continuously received parameter signals 114 and subsequently generates the feedback signal 116 based on the variations calculated from the sleepless degree parameter records of the user. In an embodiment of the present invention, audio associated data, such as a playlist or any list of audio file or streams, corresponding to the audio file or streams which are playable on the electronic device 130 is stored in the server 120 by default. Thus, the server 120 can select an audio file or stream based on the audio associated data, and generate the feedback signal 116 to control the electronic device 130 to play the selected audio file or stream. In another embodiment of the present invention, audio associated data, such as a playlist or any list of audio file or streams, is stored in the electronic device 130. The server 120 can retrieve the audio associated data from the electronic device 130 and generates the feedback signal 116 accordingly to control the electronic device 130 to play the selected audio file or stream. In another embodiment of the present invention, the server 120 can also generate the feedback signal 116 directly to request the electronic device 130 to switch the audio file or stream being played to any other audio file or stream. The electronic device 130 can switch the audio being played to other audio file or stream sequentially or randomly based on the audio file or streams stored internally. The electronic device 130 then generates a signal to notify the server 120 of the new audio file or stream to be played and the server 120 makes a corresponding record, for example, the title, source, or other associated information of the audio file or stream, for tracking.

In other words, the sleep aid system 100 is capable of learning to select suitable audio file or stream to be played. The sleep aid system 100 compares the comparison data, including past records, stored in the server 120 with a current sleepless degree parameter of a user and transmits a corresponding feedback signal 116 to the electronic device 130, so as to allow the electronic device 130 to play the most suitable audio file or stream to help the user to fall asleep. The electronic device 130 can be any device, such as a MP3 player, a speaker, a smart handheld device, a computer, or a television, etc., that is capable of playing an audio file or stream. The sleep aid system 100 of the present invention can further provide an application program which is to be installed on the electronic device 130. The application program can provide a user interface for the user. The user can browse his or her brainwave signal in real-time through the application program, obtain history records of brainwave activities and previously played audio file or streams, and retrieve evaluation results of how effective each playable audio file or stream is in aiding the user's sleep from the server 120. Furthermore, the user can edit the audio playlist or adjust the order of the audio files or streams to be played via the user interface.

Figure 1B:
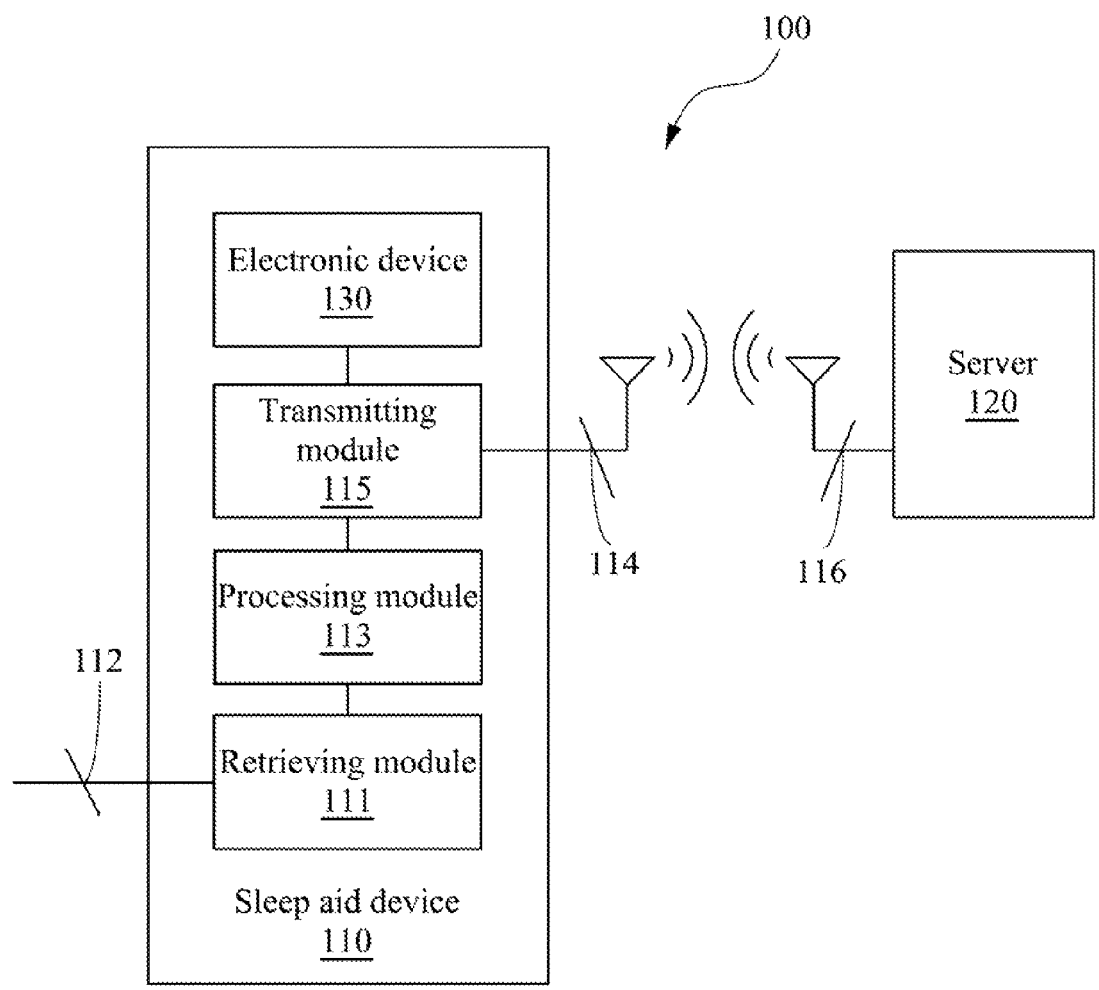
FIG. 1B is a diagram illustrating a sleep aid system according to another embodiment of the present invention.

In another embodiment of the present invention as shown in FIG. 1B, the sleep aid device 110 further includes an electronic device 130. In other words, the electronic device 130 can be an audio playback module, embedded in the sleep aid device 110, but is not limited thereto.

Moreover, the server 120 can not only transmit the feedback signal 116 to the electronic device 130 to select an audio file or stream to be played, but also utilize the feedback signal 116 to control a volume of the electronic device 130. For instance, when a user listens to the specific audio file or stream played by the electronic device 130 and becomes sleepy gradually, the server 120 will determine the user is entering into sleep according to the received parameter signal 114, and then generate and transmit a corresponding feedback signal 116 to the electronic device 130, so as to control the electronic device 130 to gradually decrease the volume of the specific audio file or stream that is played. When the user enters sleep, the server can generates corresponding feedback signal 116 which commands the electronic device 130 to stop playing the audio file or stream or enter into standby mode. In addition, when the received parameter signal 114 indicates the user's brainwave state is not in deep sleep, the server 120 can command the electronic device 130 to switch the currently played audio file or stream in order to aid the user's sleep quality. Since the feedback signal 116 is generated by the server 120 based on the received parameter signal 114, the server 120 can react to the brainwave state of the user in real-time and command the electronic device 130 accordingly, so as to assist the user to enter into sleep. Furthermore, since different audio files or streams may have different effects on different users' sleeps, the server 120 makes the history records of the parameter signal 114 received from different users, who might be in different brainwave states respectively when different audio files or streams are playing, along with the associated information of the concurrently played audio file or stream and other information of the user, for example, location, time or other identification or physiological data of the users, in order to separate the comparison data for any individual user. With this, the server 120 eventually keeps track of how different audio files or streams affect different users in different situations or states and can select the most sleep-aid effective audio file or stream to be played by electronic device 130 according to the real-time brainwave status of any user of the system.

Figure 1C:
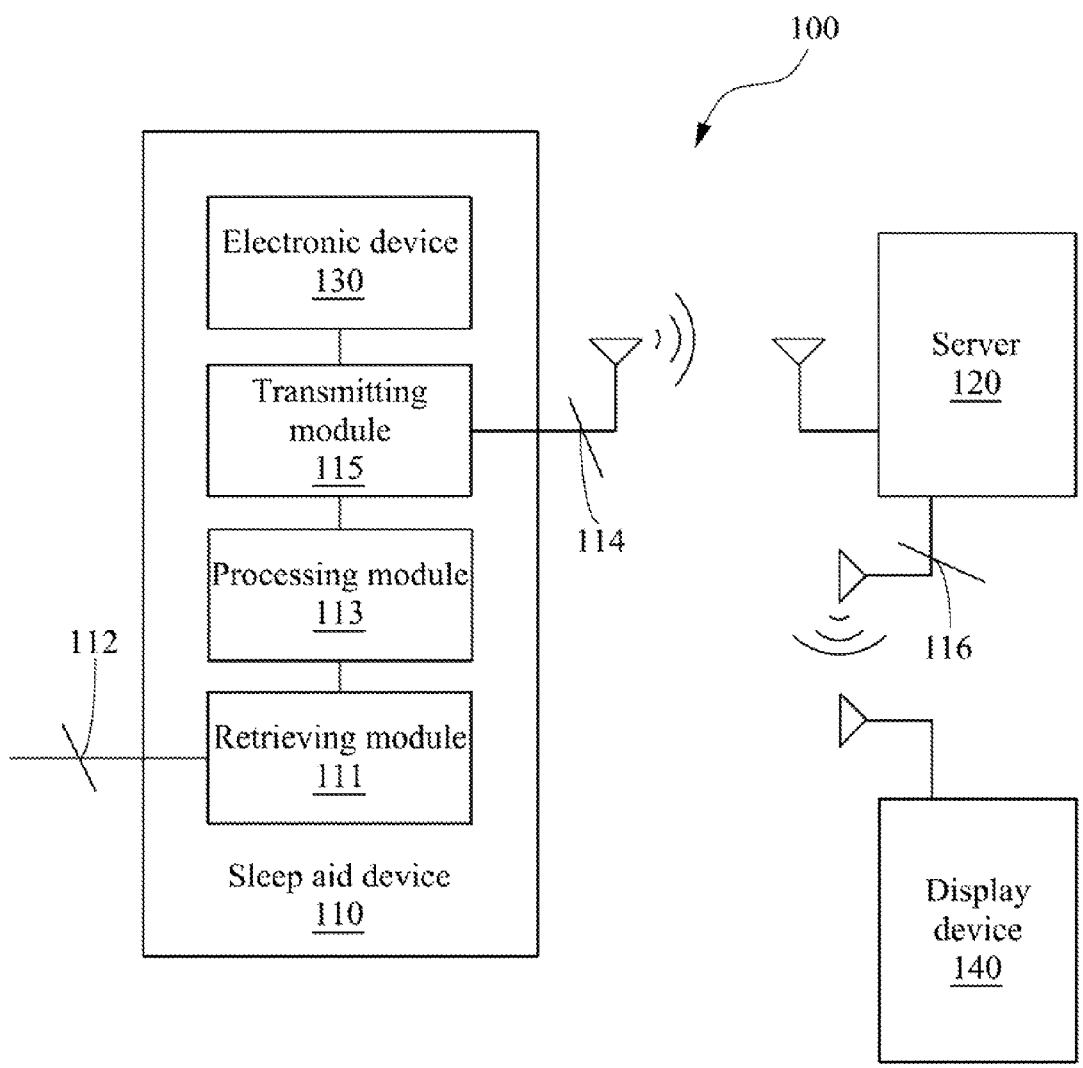
FIG. 1C is a diagram illustrating a sleep aid system according to another embodiment of the present invention.

In another embodiment of the present invention as shown in FIG. 1C, the sleep aid system 100 further includes a display device 140. For instance, some users may be used to watching television program or other video in bed and forget to turn off the television or the display device before falling asleep. The server 120 of the present invention can receive the parameter signal 114 from the transmitting module 115 and determines the state of the brainwave signal 112 from the user according to the parameter signal 114. When the server 120 determines the user is almost asleep or has fallen asleep, the server 120 generates the feedback signal 116 according to the parameter signal 114 and transmits the feedback signal 116 to the display device 140. In this manner, the display device 140 can be controlled in real-time by the server 120 to gradually dim the display brightness, stop video playback or enter into standby mode. In other words, the feedback signal 116 can include a command to set the brightness value of the display device 140, stopping video playback operation, or turning the display device 140 off.

Figure 1D:
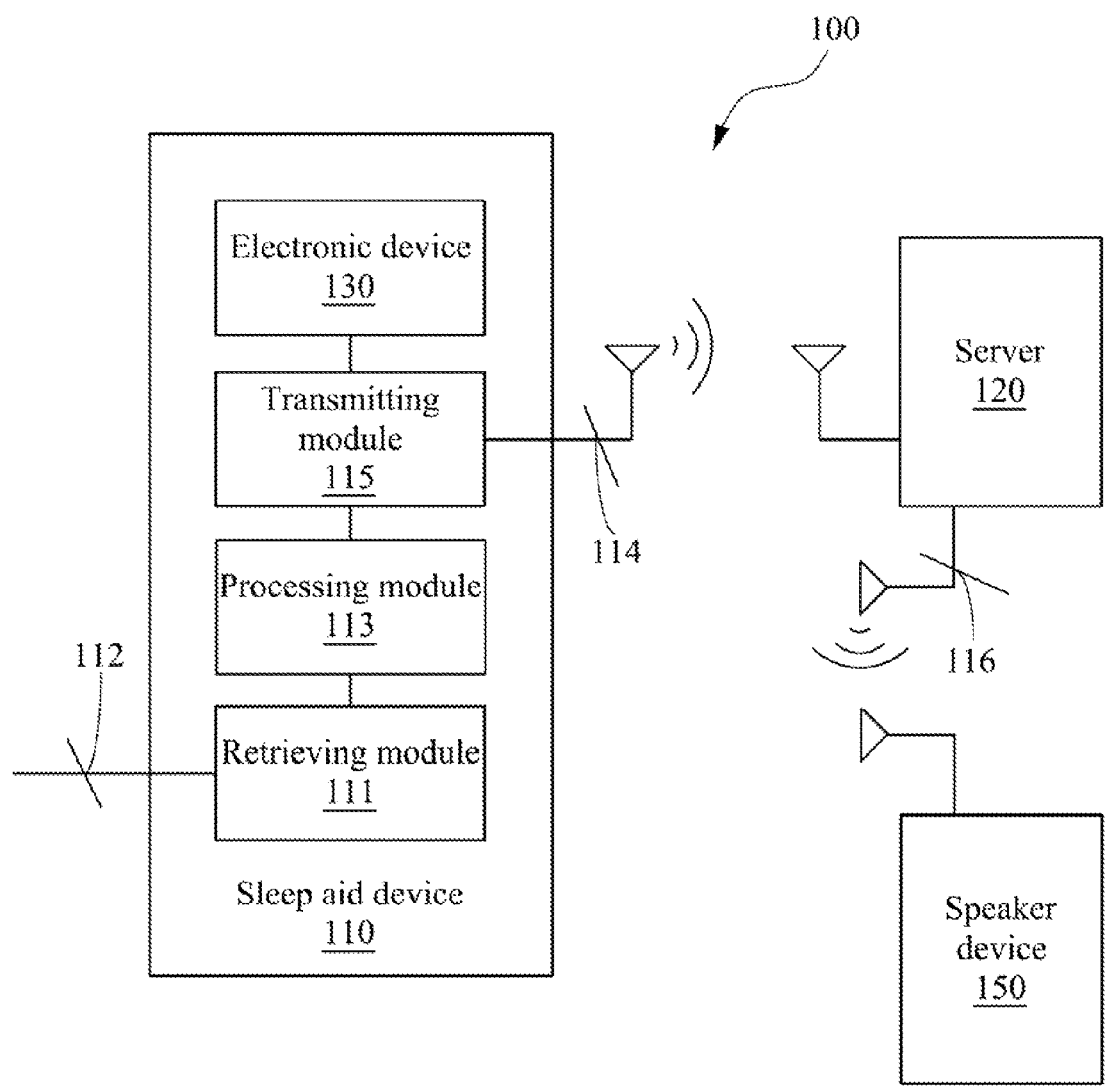
FIG. 1D is a diagram illustrating a sleep aid system according to another embodiment of the present invention.

In another embodiment of the present invention as shown in FIG. 1D, the sleep aid system 100 can further include a speaker device 150. For instance, the speaker device 150 can be utilized to play an audio file or stream, transmit data indicating the currently played audio file or stream to the server 120, receive the feedback signal 116 from the server 120, and switch the currently played audio file or stream to another audio file or stream according to the feedback signal 116. In addition, the server 120 can control the speaker device 150 to gradually lower audio playback volume, terminate playback operation of audio file or stream, or enter standby mode by transmitting the feedback signal 116 to the speaker device 150. The feedback signal 116 can include a command to turn an audio playback device, e.g. the speaker device 150, off or a command to set audio playback volume of the audio playback device.

Figure 2A:
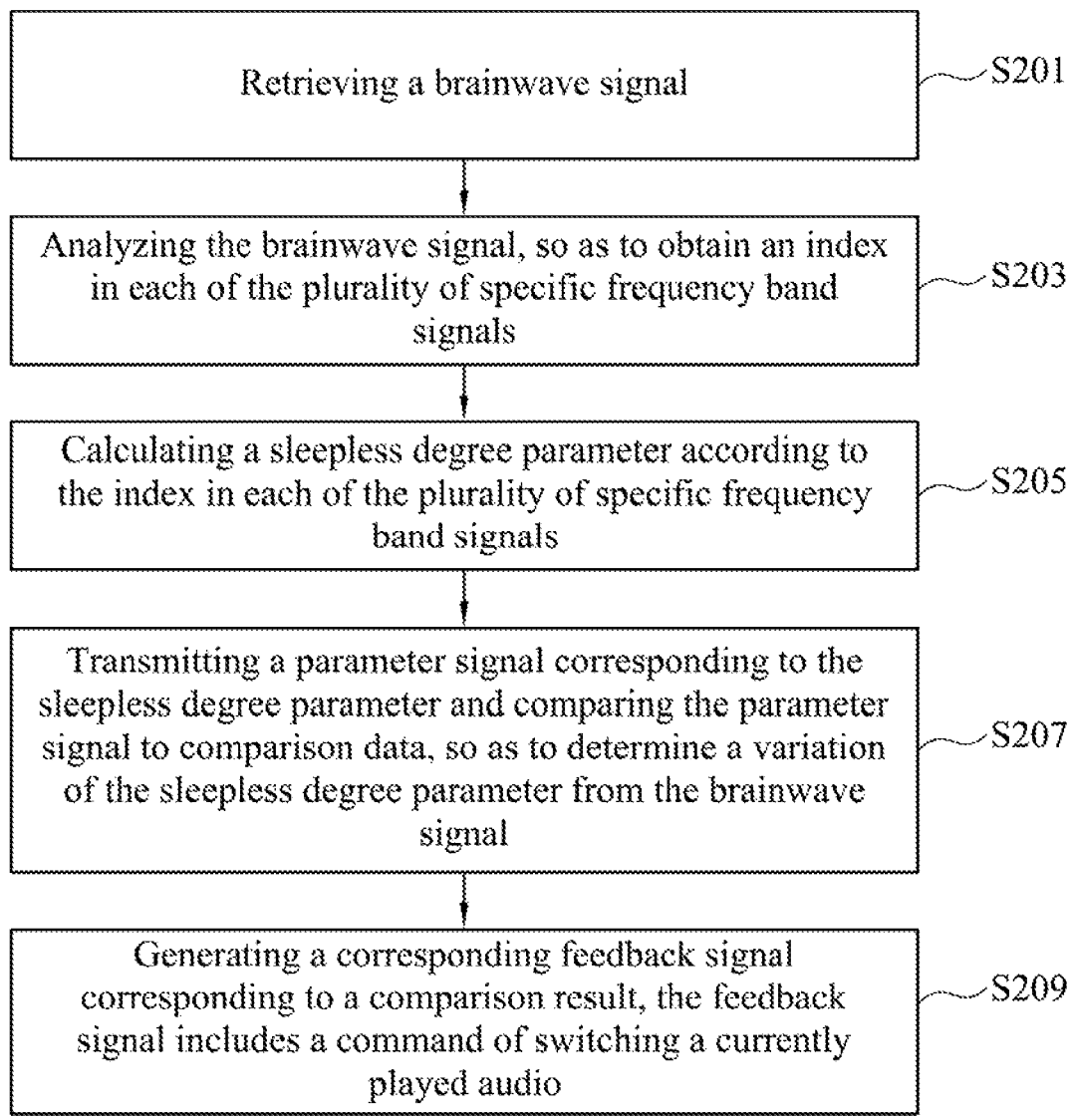
FIG. 2A is a flow chart illustrating an operation method of a sleep aid system according to an embodiment of the present invention.

Reference is now made to FIG. 2A. FIG. 2A is a flow chart illustrating an operation method 200 of a sleep aid system according to an embodiment of the present invention. The operation method 200 is further detailed below. The operation method 200 can also be applied to the above-mentioned embodiments, but is not limited thereto.

Figure 2B:
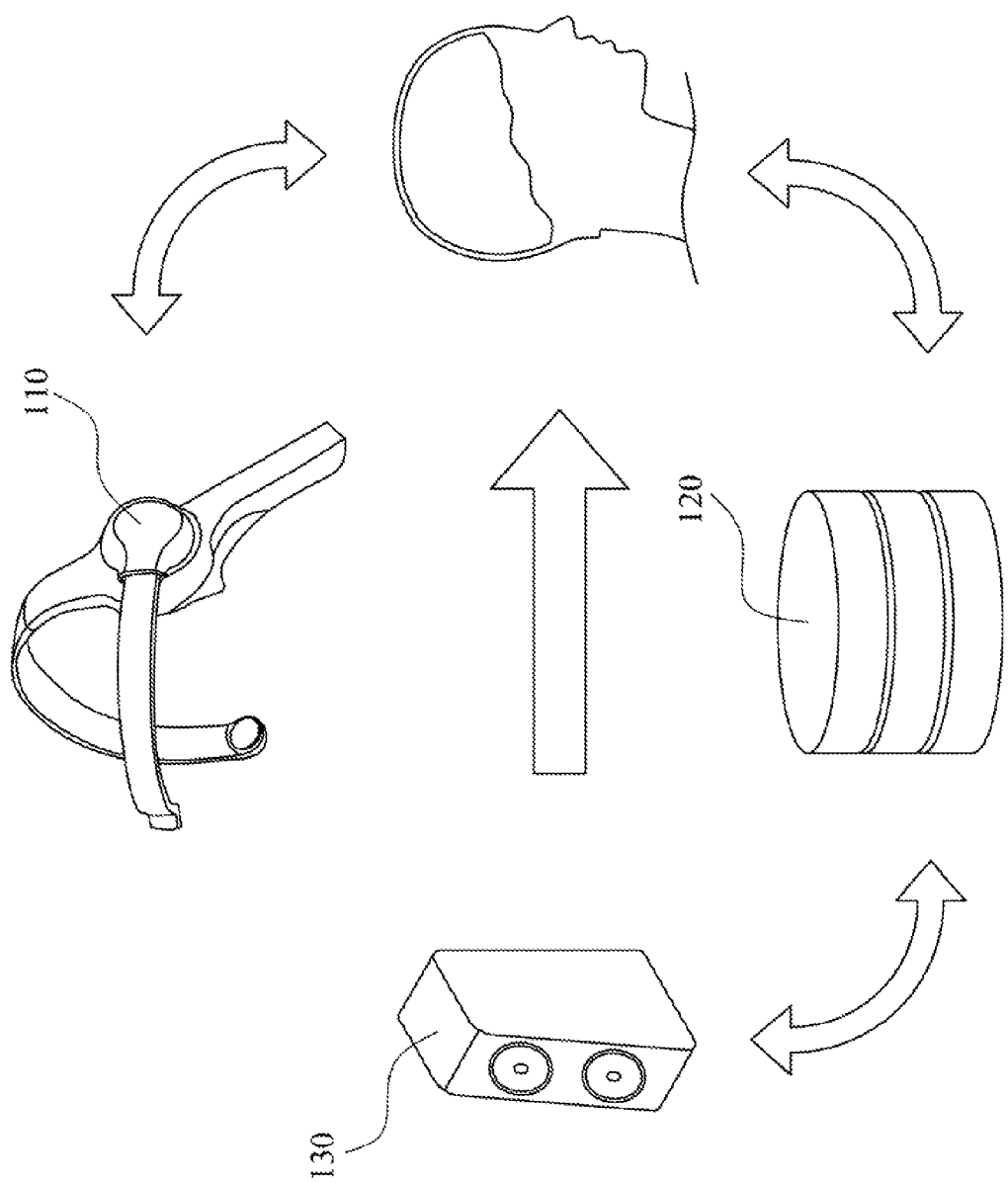
FIG. 2B is a diagram illustrating an operation of a sleep aid system according to an embodiment of the present invention.

Firstly, in step S201, a brainwave signal 112 is received by the sleep aid device 110. Please refer to FIG. 1A and FIG. 2B, where FIG. 2B is a diagram illustrating an operation of a sleep aid system according to an embodiment of the present invention. For instance, the sleep aid device 110 can be a wearable electronic device. A user can wear the sleep aid device 110 on the head, so the brainwave signal 112 of the user can be retrieved by the retrieving module 111 of the sleep aid device 110.

According to another embodiment, process of signal amplification, normalization and noise elimination on the received brainwave signal 112 can also be performed in the step S201, so as to obtain a plurality of specific frequency band signals. For instance, the brainwave signals 112 corresponds to the electroencephalography activity in the brain of the user and include at least a $\theta$ wave, an $\alpha$ wave and a $\beta$ wave. The retrieving module 111 of the sleep aid device 110 performs signal amplification, normalization and noise elimination to the retrieved brainwave signal 112 and obtains specific frequency band signals such as the $\theta$ wave, the $\alpha$ wave and the $\beta$ wave signals.

In step S203, the brainwave signal 112 is analyzed so as to obtain an index in each of the plurality of specific frequency band signals.

In specific, the processing module 113 of the sleep aid device 110 analyzes the brainwave signal 112 of the user and obtains the index in each of the plurality of specific frequency band signals of the $\theta$ wave, the $\alpha$ wave and the $\beta$ wave (e.g. shown in Table 1 above).

The sleepless degree parameter is then calculated according to the index in each of the plurality of specific frequency band signals in step S205.

Reference is now made to Table 1 and the user B used as an example. Indexes of the $\theta$ wave, the $\alpha$ wave and the $\beta$ wave in the brainwave signal 112 from the user B are measured as 5x, 6y and 3z respectively, where x, y and z are general coefficients. The processing module 113 of the sleep aid device 110 calculates the sleepless degree parameter according to the indexes of the $\theta$ wave, the $\alpha$ wave and the $\beta$ wave and determines the current state of the user's brainwave.

In step S207, a parameter signal 114 corresponding to the sleepless degree parameter is transmitted and compared to the records in comparison data, so as to determine the variation of the sleepless degree parameter from the brainwave signal 112.

For instance, the server 120 stores multiple comparison data including records of sleepless degree parameter and associated information of concurrently played audio file or stream, location, time or other identification or physiological data of different users. After the processing module 113 of the sleep aid device 110 retrieves the brainwave signal 112 from the user and then generates the parameter signal 114 according to the sleepless degree parameter of the user, the transmitting module 115 will transmit the parameter signal 114 corresponding to the sleepless degree parameter of the user to the server 120. The server 120 receives the parameter signal 114 from the transmitting module 115 and compares the parameter signal 114 to the multiple comparison data, so as to determine the variation of the sleepless degree parameter of the brainwave signal 112, which indicating the variation of the user's sleeping status.

In step S209, a feedback signal 116 corresponding to the comparison result of step S207 is then generated, wherein the feedback signal 116 may include a command to switch a currently played audio file or stream.

In specific, different audio may have different effect on each user and the sleepless degree parameters of each user are also different from others occasionally. Hence the server 120 keeps track of the parameter signal 114 from different users respectively every time the server 120 receives the parameter signal 114. In this way, the server 120 can compare the received parameter signal 114 with the kept records of the user in real-time, determine the audio file or stream that is most suitable to help the user's sleep, and control the playback device to play the determined audio file or stream. The determination process is according to how different audio files or streams affect different users with different brainwave states in records and also following different users favorite settings. If the determined audio file or stream is different from the currently played audio file or stream, the server 120 then transmits a corresponding feedback signal 116 to the electronic device 130 in order to control the electronic device 130 to play the audio file or stream recommended by the server 120 to aid the users sleep. In other words, the server 120 generates the corresponding feedback signal 116 according to the comparison result, where the feedback signal 116 includes a command to switch a currently played audio file or stream to another audio file or stream. In an embodiment of the present invention, the server 120 determines a specific audio file or stream, which is most effective to the user, according to the comparison data and the parameter signal 114, and then generates the corresponding feedback signal 116 accordingly, where the feedback signal 116 includes a command to switch a currently played audio file or stream to the specific audio file or stream. In another embodiment of the present invention, the server 120 can just skip the determination process of the specific audio file or stream and generate the feedback signal 116 directly to request the electronic device 130 to switch the currently played audio file or stream to any audio other file or stream. After receiving such feedback signal 116, the electronic device 130 can sequentially or randomly pick an audio file or stream to be played. The electronic device 130 then generates a signal to notify the server 120 of which new audio file or stream is selected to be played.

In another embodiment, the operation method 200 further include the step for making a record of the transmitted sleepless degree parameter and the concurrently played audio file or stream according to the parameter signal 114.

For instance, a user may wear the sleep aid device 110 in different scenarios, which include the time and location where the user is, the mind status of the user, the currently played audio file or stream and other environment conditions. The server 120 keeps track of the user's sleepless degree parameters based on the scenario of the user and the corresponding audio file or stream being listened by the user simultaneously. Based on the kept records and transmitted sleepless degree parameters, the variation of the user's brainwave state can be calculated in real-time in order to measure how the playing audio file or stream affect the user's sleep in certain scenario and the corresponding feedback signal 116 for aiding the user's sleep can be generated accordingly. When it is detected that the user has listened to an audio file or stream for a period of time but still cannot enter the sleep state or his sleepless degree parameter has not decreased, the feedback signal 116 will be generated to switch the audio file or stream to be played. Furthermore, no matter how long the user has listened to the currently played audio file or stream, when it is detected that the sleepless degree parameter of the user has changed towards a more sober state for a certain degree, the feedback signal 116 will also be generated to switch the audio file or stream to be played. The associated information of all played audio files or streams are kept in record along with the concurrent brainwave state represented by the sleepless degree parameters, so when the sleep aid system determines which audio file or stream should be played, priorities of the audio files or streams that are less effective in aiding the user's sleep will be lowered in the determination process based on the history records. Hence any audio tile or stream with a lower priority will be prevented from being played firstly. Furthermore, it is possible that different audio files or streams have different effects on an individual user when he or she is in different sleepless degree categories. So the sleep aid system may select the most suitable audio file or stream to be played in different situations or scenarios of the user based on the past records of similar situations or scenarios, so as to achieve better effects. Since the sleep aid system of the present invention keeps a record of the associated information of all the audio files or streams have been played and the variations of the user's brainwave state corresponding to the concurrently played audio files or streams, the sleep aid system can always select the audio file or stream which is most effective in aiding the user's sleep based on the past records.

The abovementioned steps are not recited in the sequence in which the steps are performed. Unless the sequence of the steps is expressly indicated, the order of the steps is interchangeable, and all or part of the steps may be simultaneously, partially simultaneously, or sequentially performed in the method of the present invention.

In another embodiment, the sleep aid system 100 can further include a display device 140, and the operation method 200 of the present invention can further include a step for transmitting the feedback signal 116 to the display device 140, in order to control the display device 140 gradually dim display brightness according to the feedback signal 116.

Please refer to FIG. 1C where the display device 140 can be a television. When a user is wearing the sleep aid device 110 and watching television program, the sleep aid device 110 detects the brainwave state of the user and transmits the parameter signal 114 to the server 120. The server 120 transmits the feedback signal 116 to the television according to the processed result of the received parameter signal 114. When the parameter signal 114 indicates the user starting to enter into sleep, the feedback signal 116 controls the television to gradually dim the display brightness. When the user is asleep, the server 120 transmits the feedback signal 116 to turn off the television, which is generated according to the processed result of the received parameter signal 114. In one embodiment scenario of the present invention, the display device 140 can also be a MP3 player, a smart handheld device, a computer, a television or any device with a display component and function.

In another embodiment of the present invention, the sleep aid system 100 can further include a speaker device 150. The operation method 200 can further include a following step for transmitting the feedback signal 116 to the speaker device 150 and controlling the speaker device 150 lower audio volume gradually, wherein the feedback signal 116 is generated according to the processed result of the received parameter signal 114.

Reference is now made to FIG. 1D where the speaker device 150 can be included in a television. When a user is wearing the sleep aid device 110 and listening to music or audio from the television, the sleep aid device 110 can detect the brainwave state of the user and transmit the parameter signal 114 to the server 120. The server 120 then generates and transmits the feedback signal 116 to the television according to the parameter signal 114. When the user starts to enter into sleep, the feedback signal 116 is generated to control the television to gradually lower the music or audio volume of the television. When the user is asleep, the server 120 transmits the feedback signal 116 to turn off the television according to the parameter signal 114. In one embodiment scenario of the present invention, the speaker device 150 can also be a MP3 player, a smart handheld device, a computer, a television, a speaker or any device with an audio playback component and function.

Figure 3:
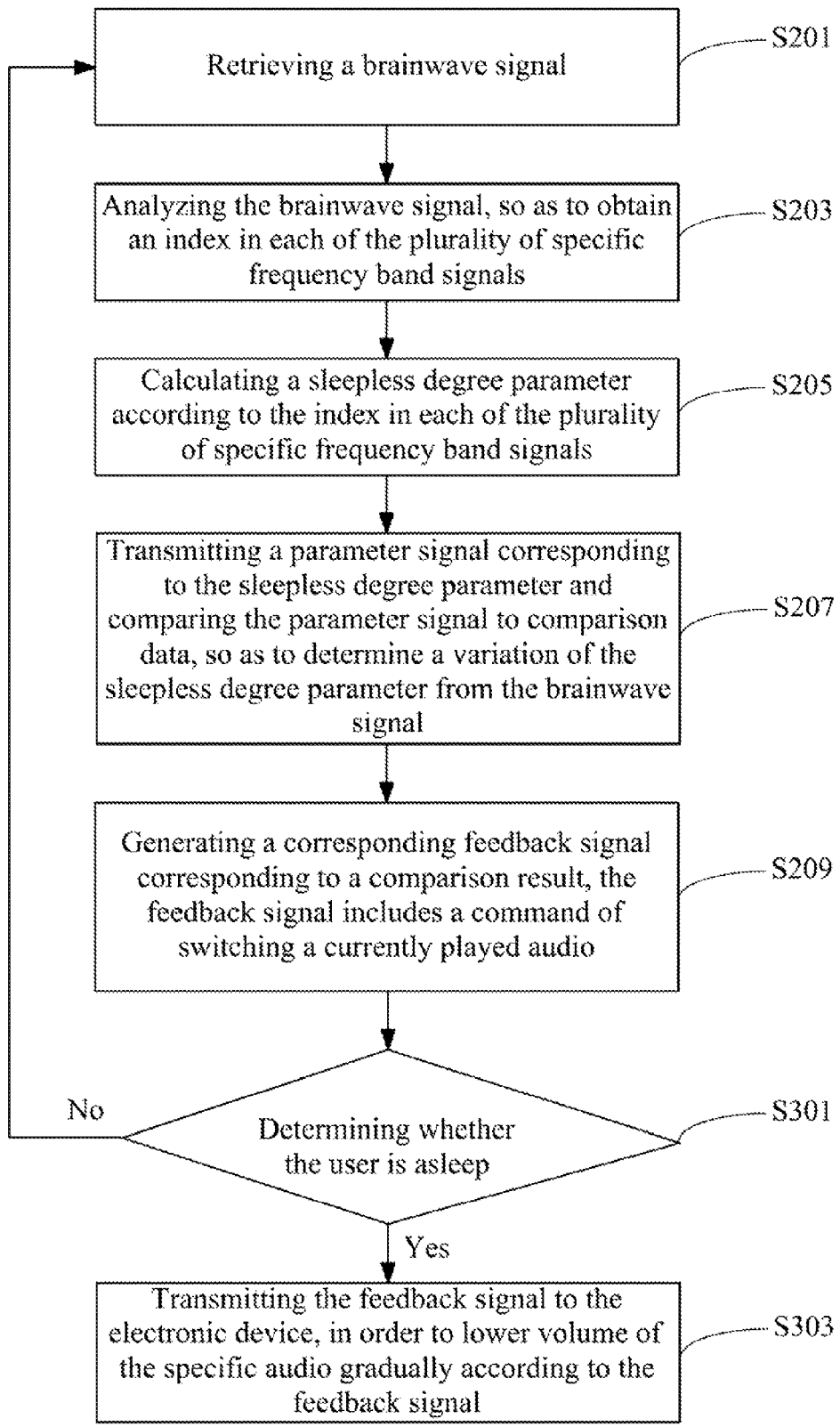
FIG. 3 is a flow chart illustrating an operation method of a sleep aid system according to another embodiment of the present invention.

Reference is now made to FIG. 3. FIG. 3 is a flow chart illustrating an operation method 300 of a sleep aid system according to an embodiment of the present invention. In addition to steps S201, S203, S205, S207 and S209, the operation method 300 further includes steps S301 and S303. Steps S201, S203, S205, S207 and S209 have been explained in previous embodiments so relative descriptions are omitted hereinafter.

Subsequent to step S209, step S301 is performed for determining whether the user is asleep.

For instance, a user may wear the sleep aid device 110 in different scenarios, and the server 120 will keep track of the user's sleepless degree parameters based on the scenario of the user and the corresponding audio file or stream being listened by the user simultaneously. Based on the parameter signal 114 corresponding to the sleepless degree parameters, the server 120 can determine whether the user is asleep. If the user is not asleep, the retrieving module 111 of the sleep aid device 110 keeps retrieving the brainwave signal 112 of the user, and transmits the processed parameter signal 114 to the server 120, so the server 120 will continuously keep track of the sleepless degree parameters of the user and the corresponding audio file or stream listed by the user simultaneously. The server 120 then generates and transmits the corresponding feedback signal 116 to the electronic device 130, so the electronic device 130 is controlled to play the most suitable audio file or stream to help the user's sleep.

Subsequently, step S303 is then performed to transmit the feedback signal 116 to the electronic device, in order to lower audio volume of the electronic device according to the feedback signal 116.

For instance, when the user is wearing the sleep aid device 110 and listening to the audio file or stream played by the electronic device 130, the sleep aid device 110 can detect the brainwave state of the user and transmit the parameter signal 114 to the server 120. The server 120 then generates and transmits the feedback signal 116 to the electronic device 130 according to the parameter signal 114. When the user starts to enter into sleep, the correspondingly feedback signal 116 generated by the server 120 will control the electronic device 130 to gradually lower the audio volume of the electronic device 130. When the user is asleep, the server 120 will generate the feedback signal 116 and control the electronic device 130 to terminate or turn off the audio playback operation according to the received parameter signal 114 which corresponds to the brainwave signal 112 of the user.

From the above-mentioned embodiments, the sleep aid system and the operation method of the present invention can automatically select the most suitable audio to help a user's sleep according to the brainwave signal of the user. The sleep aid system of the present invention keeps track of the user's usage condition in real-time for determining the user's sleep state and generating feedback signals accordingly, in order to aid the user's sleep. Furthermore, the sleep aid system and the operation method of the present invention can also control or tune devices that are ambient to the user. When the user is sleepy, the brainwave signal of the user will make the sleep aid system gradually decrease the brightness of display or audio volume of the electronic device nearby, so as to help the user fall asleep. The sleep aid system of the present invention can be adjusted or modified according to practical needs. For instance, the server 120 can be any electronic device that is capable of performing calculation and communication. If the sleep aid system is designed for personal use only, the server 120 can be integrated within the electronic device 130. In addition, the communication protocol utilized by the sleep aid system can be adjusted or selected according to communication transmission distance and the number of users. If the number of users is limited and the users are all within a same building, the server 120 can be a personal computer or any applicable device that is capable of performing data transmission, storage, comparison and other related programs. The server 120 can communicate with the sleep aid device by utilizing a short-range communication protocol, such as Wi-Fi or Bluetooth, etc. If there are a large number of users using the system and communicating over very long distances, the server 120 must at least include a central server that can handle a large amount of calculations simultaneously and utilizes the communication technology that has a wide coverage. In addition, if the sleep aid system of the present invention is designed for only one user, certain functions such as data calculation and data comparison of the server 120 can be performed by corresponding software instead, for example, an application executed in any personal computing device. Hence components of the server 120 can be integrated within the electronic device 130 or the sleep aid device 110 and become a single device. In this way, the sleep aid system of the present invention can aid the users sleep directly without requiring the transmitting module 115 to transmit or receive data or signals to or from any remote server or device. Since the software application provided by the sleep aid system of the present invention can be installed in any computing device with playback or control functions to perform operations and processes of the server 120 or the electronic device 130 in the above-mentioned embodiments, the sleep aid system of the present invention is only required to provide the sleep aid device 110 and the corresponding application compatible with the electronic device which already belongs to the user, such as mobile phone, laptop, personal computer, tablet, or any computing device, in order to perform sleep aiding functions.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sleep aid system, comprising:
   a sleep aid device, comprising:
   a retrieving module, wherein the retrieving module retrieves a brainwave signal of a user and the brainwave signal comprises a plurality of specific frequency band signals;
   a processing module, wherein the processing module analyzes the brainwave signal in order to obtain an index in each of the plurality of specific frequency band signals, and the processing module calculates a sleepless degree parameter according to the index in each of the plurality of specific frequency band signals, wherein the sleepless degree parameter represents one of at least five brainwave states before entering into sleep; and
   a transmitting module, wherein the transmitting module transmits a parameter signal corresponding to the sleepless degree parameter; and
   a server, wherein the server receives the parameter signal from the transmitting module, the server stores a multiple sets of comparison data, the server compares the parameter signal to the comparison data and generates a first feedback signal according to a comparison result, and the first feedback signal comprises a command to switch an audio file or stream which is currently being played to other audio file or stream to aid the user to enter into sleep,
   wherein the other audio file or stream is selected with respect to help the user enter into sleep.

2. The sleep aid system of claim 1, wherein the command to switch the audio file or stream which is currently being played to other audio file or stream is a command to play a specific audio file or stream, and the specific audio file or stream is determined by the server based on the comparison data and the parameter signal.

3. The sleep aid system of claim 1, further comprising:
   an electronic device playing an audio file or stream, wherein the electronic device transmits audio associated data to the server and receives the first feedback signal from the server, and the electronic device switches the currently played audio file or stream according to the first feedback signal.

4. The sleep aid system of claim 1, wherein the server generates a second feedback signal when the brainwave signal is determined as entering an asleep state, and the second feedback signal comprises a command to turn off a display device.

5. The sleep aid system of claim 1, wherein the server generates a second feedback signal when the brainwave signal is determined as entering an almost asleep state, and the second feedback signal comprises a command to gradually dim the brightness of a display device.

6. The sleep aid system of claim 1, wherein the server generates a second feedback signal when the brainwave signal is determined as starting to entering into sleep, and the second feedback signal comprises a command to gradually lower an audio volume of a speaker.

7. The sleep aid system of claim 1, wherein the server generates a second feedback signal when the brainwave signal is determined as entering an asleep state, and the second feedback signal comprises a command to terminate an audio playback operation.

8. A sleep aid system, comprising
   a sleep aid device, comprising:
   a retrieving module, wherein the retrieving module retrieves a brainwave signal and the brainwave signal comprises a plurality of specific frequency band signals;
   a processing module, wherein the processing module analyzes the brainwave signal in order to obtain an index in each of the plurality of specific frequency band signals, and calculates a sleepless degree parameter according to the index in each of the plurality of specific frequency band signals, wherein the sleepless degree parameter represents one of at least five brainwave states regarding before entering into sleep; and
   a transmitting module, wherein the transmitting module transmits a parameter signal corresponding to the sleepless degree parameter to a server; and
   an electronic device playing an audio file or stream, wherein the electronic device transmits audio associated data to the server and receives a first feedback signal from the server, and the electronic device switches a currently played audio file or stream to other audio file or stream according to the first feedback signal to aid the user to enter into sleep,
   wherein the other audio file stream elected with respect to help the user enter into sleep.

9. The sleep aid system of claim 8, further comprising:
   a server, wherein the server receives the parameter signal from the transmitting module, the server stores a multiple sets of comparison data, the server compares the parameter signal to the comparison data and generates the first feedback signal according to a comparison result, and the first feedback signal comprises a command to switch an audio file or stream which is currently being played to other audio file or stream.

10. The sleep aid system of claim wherein the first feedback signal comprises a command to play a specific audio file or stream and the specific audio file or stream is determined by the server based on the parameter signal.

11. The sleep aid system of claim 8, wherein the electronic device receives a second feedback signal from the server and the second feedback signal comprises a command to turn of a display on the electronic device.

12. The sleep aid system of claim 8, wherein the electronic device receives a second feedback signal from the server and the second feedback signal comprises a command to gradually dim the brightness of a display on the electronic device.

13. The sleep aid system of claim 8, wherein the electronic device receives a second feedback signal from the server and the second feedback signal comprises a command to gradually lower an audio volume of the electronic device.

14. The sleep aid system of claim 8, wherein the electronic device receives a second feedback signal from the server and the second feedback signal comprises a command to terminate an audio playback operation of the electronic device.

15. A sleep aid system, comprising:
   a sleep aid device, comprising:
   a retrieving module, wherein the retrieving module retrieves a brainwave signal and the brainwave signal comprises a plurality of specific frequency band signals;
   a processing module, wherein the processing module analyzes the brainwave signal in order to obtain an index in each of the plurality of specific frequency band signals, and calculates a sleepless degree parameter according to the index in each of the plurality of specific frequency band signals, wherein the sleepless degree parameter represents one of at least five brainwave states regarding before entering into sleep; and a transmitting module, wherein the transmitting module, transmits parameter signal corresponding to the sleepless degree parameter; and a server, wherein the server receives the parameter signal from the transmitting module, the server determines a state of the brainwave signal according to the parameter signal, wherein the server generates a first feedback signal when the brainwave signal is determined as entering an asleep state, and the first feedback signal comprises a command to turn off a display device.

16. The sleep aid system of claim 15, wherein the server generates a second feedback signal when the brainwave signal is determined as entering an almost asleep state, and the second feedback signal comprises a command to gradually dim the brightness of the display device.

17. The sleep aid system of claim 15, wherein the server generates a second feedback signal when the brainwave signal is determined as starting to entering into sleep, and the second feedback signal comprises a command to gradually lower an audio volume of a speaker.

18. The sleep aid system of claim 15, wherein the server generates a second feedback signal when the brainwave signal is determined as entering an asleep state, and the second feedback signal comprises a command to terminate an audio playback operation.

19. The sleep aid system of claim 15, wherein the server stores a multiple sets of comparison data, the server compares the parameter signal to the comparison data and generates a second feedback signal according to a comparison result, and the second feedback signal comprises a command to switch an audio file or stream which is currently being played to other audio file or stream.

20. The sleep aid system of claim 19, wherein the command to switch the audio file or stream which is currently being played to other audio file or stream is a command to play a specific audio file or stream, and the specific audio file or stream is determined by the server based on the comparison data and the parameter signal.

* * * * *